United States Patent [19]

Ishida et al.

[11] 4,354,936

[45] Oct. 19, 1982

[54] ANAEROBIC DIGESTION PROCESS

[75] Inventors: Masahiko Ishida; Ryoichi Haga; Yoji Odawara, all of Hitachi, Japan

[73] Assignee: The Agency of Industrial Science and Technology, Tokyo, Japan

[21] Appl. No.: 241,056

[22] Filed: Mar. 6, 1981

[30] Foreign Application Priority Data

May 20, 1980 [JP] Japan .................................. 55-65909

[51] Int. Cl.³ .............................. C02F 3/28; C02F 3/32
[52] U.S. Cl. ...................................... 210/602; 210/603; 210/605; 210/631; 210/170; 48/197 A; 47/1.4
[58] Field of Search ............... 210/602, 603, 170, 605, 210/631; 48/197 A; 47/1.4

[56] References Cited

U.S. PATENT DOCUMENTS

| 4,057,401 | 11/1977 | Boblitz | 210/603 |
| 4,076,515 | 2/1978 | Rickard | 210/603 |
| 4,134,830 | 1/1979 | Skogman et al. | 210/603 |
| 4,209,388 | 6/1980 | De Fraites | 210/170 |
| 4,213,857 | 7/1980 | Ishida et al. | 210/603 |
| 4,267,038 | 5/1981 | Thompson | 210/170 |

FOREIGN PATENT DOCUMENTS 801144 9/1958 United Kingdom ............... 210/603

Primary Examiner—Benoit Castel
Attorney, Agent, or Firm—Birch, Stewart, Kolasch & Birch

[57] ABSTRACT

Methane gas produced according to an anaerobic digestion of organic wastes is introduced into digested separated water which is alkalized by a photo-culture of algae, whereby impurity carbon dioxide gas is removed by absorption. Accordingly, methane of high concentration is recovered and at the same time, by-product algae is recycled as feedstock, and thereby improving the yield of methane.

16 Claims, 1 Drawing Figure

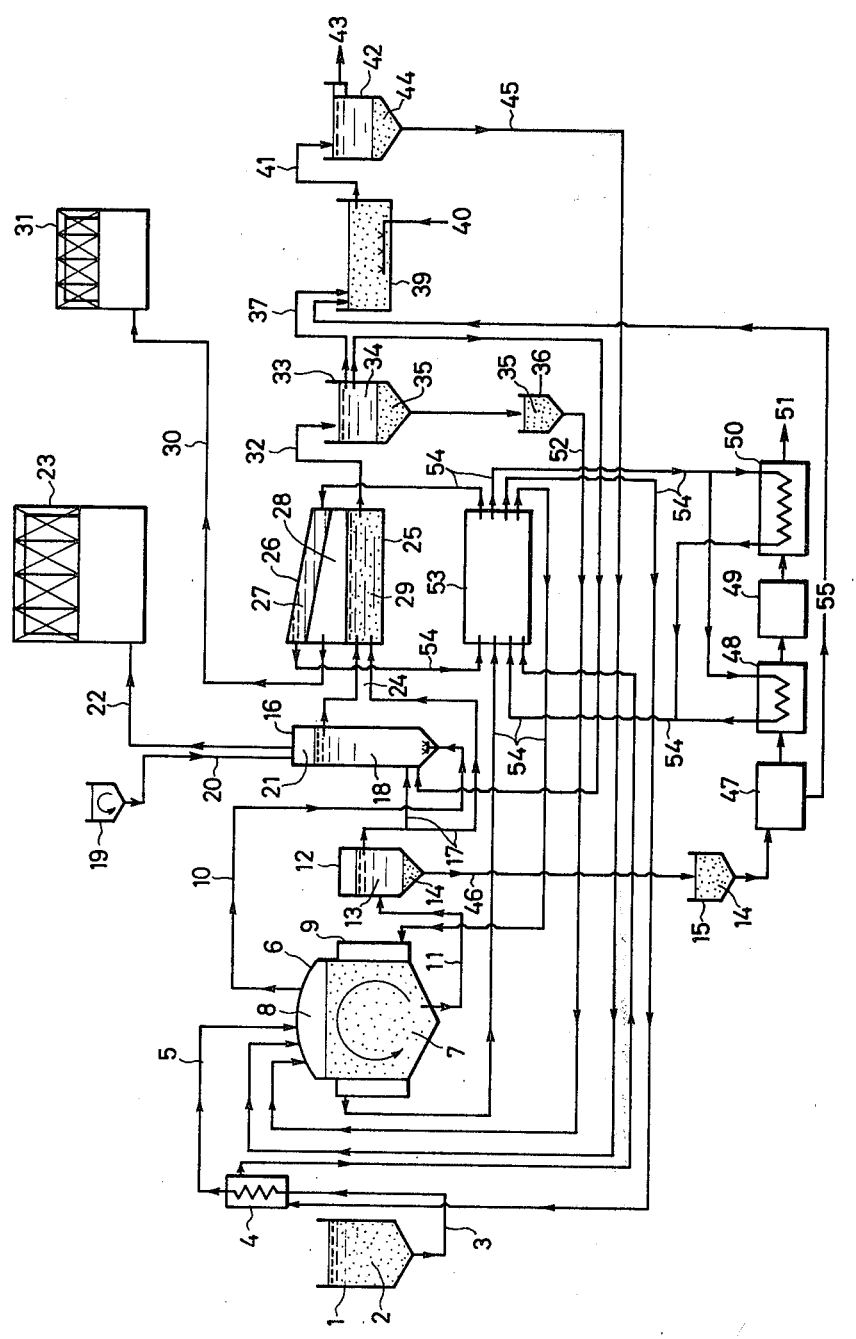

ANAEROBIC DIGESTION PROCESS

BACKGROUND OF THE INVENTION

The present invention relates to a process for the treatment of organic wastes, and more particularly to an improved anaerobic digestion process for the treatment of organic wastes which results in the efficient recovery of high purity methane, hydrogen and oxygen.

Heretofore, organic wastes, such as excess activated sludge and human waste have been treated primarily by employing an anaerobic digestion process. Recently, city garbage is being treated by an anaerobic digestion process.

It is known that anaerobic digestion proceeds primarily by combining two reactions. One reaction is liquefaction fermentation by a facultative anaerobic bacteria (liquefying bacteria group) in which organic substances in the wastes are converted into lower molecular weight substances and decomposed volatile fatty acid. The other reaction is gasification fermentation by an obligatory anaerobic bacteria (gasifying bacteria group) in which fatty acids produced in said former reaction are converted into methane. In, in the usual mixed fermentation system, treatment is conducted for a long period of time (as long as from 20 to 50 days) in the presence and coexistence of the two above-mentioned bacteria groups in the same digester. As one method for shortening the number of days in the treatment period, a method for digesting in two separate as liquefaction fermentation and gasification fermentation steps is under testing. In the former one step process, the gas generated in the course of the fermentation consists mainly of methane and carbon dioxide containing hydrogen sulfide as a minor constituent. In the latter two step process, a mixed gas of carbon dioxide and hydrogen is produced at the liquefaction fermentation step, while in the gasification fermentation step, the same gas as in the one step process is produced, said gas containing methane and carbon dioxide and also containing a minor quantity of hydrogen sulfide. While the concentration of methane and hydrogen in these gases varies according to the feedstocks and the conditions of fermentation (condition of digestion), the concentration of methane in the methane containing gas is in the range from 45% to 70%, and as to the hydrogen containing gas it is in the range from 20% to 60%.

Conventionally, the methane gas produced by anaerobic digestion has been used not only for internal use as fuel for digestion as well as for power of agitation, but also for fuel for electric power generation. However in winter, the amount of internal consumption increases, and auxiliary fuel must also be consumed often. It is predicted that the total amount of recovered methane gas will increase in the near future due to the increase of the treating of wastes, such as sewage sludge and kitchen garbage. However, if the concentration of the methane is not enriched, the use thereof will be limited strongly as compared to high calorie gas, such as natural gas and synthetic gas from petroleum. Accordingly, it is necessary to recover the methane gas in high purity. Although, there are processes, such as a process to remove carbon dioxide under high pressure and to wash it with alkaline water, such processes are costly and are not practical. Further, the gas generated in the course of the fermentation contains hydrogen sulfide in a range between tens to hundreds ppm, and therefore, before use the hydrogen sulfide must be removed through desulfurization tower filled with desulfurization reagents and then be stored. It is known that digested sludge treated by anaerobic digestion is a good fertilizer, but when it is in the form of a slurry as it is discharged or in the form of a dehydrated cake, it has drawbacks in preservation and in transportation, and therefore, the usable area for the sludge is limited. Accordingly, manufacturing treatment such as drying and granulation, which requires new heat source, is necessary when the sludge is to be used as a fertilizer. Besides, since the concentration of BOD in the digestion treated liquid is as high as from thousands to 15 ppm, it is discharged after activated sludge treatment, and the treatment of the separated water is cumbersome. Furthermore, in the separated water, nitrogen is present in hundred ppm in the form of ammonia and phosphor is present in tens ppm in the form of phosphoric acid. Removal of such substances by activated sludge treatment is difficult. However, the water is richly nutritive.

SUMMARY OF THE INVENTION

One object of the present invention is to provide an anaerobic digestion process which eliminates the aforementioned drawbacks in the conventional anaerobic digestion processes. Other objects are to improve the energy efficiency of the process, to raise the purity of the recovered gases to improve the efficiency in the process for removing the hydrogen sulfide, to increase the added value of the digested sludge fertilizer and to treat the waste water as a perfect non-polluting process.

In the first characteristic feature of the present invention, only at the time of the starting, calcium hydroxide is added to the digested separated water until the water is alkaline. Then, fermented gas is passed through the water resulting in absorption of carbon dioxide and hydrogen sulfide. Then, culture of the photo-synthesis algae is effected by using the separated water which contains dissolved carbon dioxide. The algae body is then returned to a digester as feedstock for anaerobic digestion. The algae culture is then separated from the water and removed therefrom. The water, which has been alkalized due to the reduction of the carbonic acid concentration during the photo-synthesis action of the algae, is returned to the fermentation gas washing tower and recycled for use as gas washing water. As a result, not only the carbon dioxide but also the hydrogen sulfide gas is removed therefrom, and it is possible to recover the methane in a high concentration exceeding 90% along with hydrogen. Therefore, it is unnecessary to provide separate desulfurization equipment which has been conventionally required before storing the methane gas. Also, oxygen in a purity greater than 70% can be recovered from the photo-synthesis process. As the excess algae body is returned to the digester for re-use as feedstock, the yields of methane and hydrogen can be improved by 20-50%. In the photo-synthesis process, 85-95% of the BOD in the separated water is removed therefrom, and it is possible not only to treat the activated sludge directly without diluting but also to remove nitrogen and phosphorus which are difficult to remove by activated sludge treatment.

In a second characteristic feature of the present invention, light filtered through a layer of depickled water is employed as a light source for photo-synthesis of the separated water. This makes is possible to avoid a temperature rise due to excessive heat absorption, to control the temperature of the photosynthesis to an optimum range, to utilize effectively heat recovered in the depickled water layer for a heat source to heat the feedstock, to maintain the temperature of the digester, and to dry the digested sludge in the drying step.

The following, detailed description of the present invention is made by reference to the attached drawing and examples, however, various improvements and modifications are possible without departing from the scope of the present invention.

BRIEF DESCRIPTION OF THE DRAWING

The sole FIGURE of the drawing is a flow-sheet for the organic waste treatment process of the present invention.

DETAILED DESCRIPTION OF THE INVENTION

The drawing illustrates one example of the process of the present invention, as will be discussed hereinafter.

Initially, in feedstock organic waste tank 1, feedstock organic wastes 2, such as excess cultivated sludge, human/animal feces, alcohol distillery waste, wastes from various foods and agricultural products processing industries, are subjected to pulverizing treatment if necessary, formed into a slurry, and then heated with a heat exchanger 4. The heating temperature varies according to the capacity of the heat exchanger, digestion temperature, charging speed of the feedstock, and the heating capacity of the digester, neverthless, it is desirable to limit the highest temperature to 5° C. above the fermentation temperature, because the fermentation caused by an anaerobic bacterium is strongly inhibited at a temperature higher than the most suitable fermentation temperature.

Next, the feedstock which has been heat treated, is charged into the digester 6 continuously or intermittently and subjected to contact with facultative anaerobic bacteria and with obligatory anaerobic bacteria. Then it is allowed to digest anaerobically for a period of several days to several weeks under anaerobic conditions while it is continuously stirred and maintained at a constant temperature. In the fermentation process a, suitable temperature is 30°–75° C. and a suitable pH is 6.5–7.5. There parameters can be selected depending on the nature of the feedstock and the culturing temperature of the bacteria utilized. Useful facultative anaerobic bacteria are, for example, conventionally used bacteria such as Clostridium, Bacillus, Escherichia or Staphylococcus, and useful obligatory anaerobic bacteria are, for example, conventionally used bacteria such as Methanosarcina, Methanococcu or Methanbacterium. The main ingredients of the gas generated are methane 45–70% and carbon dioxide 30–55% with small amounts of hydrogen sulfide, nitrogen and hydrogen. The concentration of the hydrogen sulfide varies widely depending on the variety of feedstock and is generally in the range of fifty to hundreds ppm.

The digested slurry removed from the digester is charged into solid/liquid separator 12 for sedimentation separation and separated into digested sludge slurry 14 and digested separated liquid 13. The digested separated water is introduced to digested gas washing tank 16 through pipe 17, and only at the time of starting added with calcium hydroxide from calcium hydroxide slurry storage tank 19 for adjusting to an alkaline pH of 7.5–10. The fermented gas is blown into this alkaline separated liquid through pipe 10 and the carbon dioxide gas and hydrogen sulfide are removed by dissolution. The methane gas 21, from which the carbon dioxide and hydrogen sulfide is removed, is transferred to methane storage tank 23 through pipe 22. As a result of above blowing of the digested gas, the pH of the liquid is lowered to 7.2–8.0.

Next, digested gas washed separated water is introduced into algae culture tank 25 through pipe 24. In the tank, aquatic algae is cultured at pH 7.5–8.5 with the aid of a light source through water layer filter 26 of depickled water 27, and consequently, $BOD_5$, carbon dioxide, nitrogen, and phosphorus contained in the separated water are absorbed therein and the algae is propagated. Although the culturing conditions such as culturing temperature and stirring can be suitably selected according to the kind of the algae, the most suitable culturing temperature is 30°–40° C. Furthermore, concerning the fermentation temperature, it is possible to control the temperature to not rise above 40° C. even when sunlight is used, because of the fact that the light filter of a depickled water layer is employed. As to the algae to be used, green algae, such as Tetraspoclales, Oedogoniaceae, Zygnematales etc., blue-green algae, such as Chroococcales, Oscillaloriales etc., and other algae such as Euglenoida etc. are useful. It suitable to use algae which is resistive to water corrosion, however, the algae can be selected suitably according to the photo-culturing conditions such as the nature of the separated water, load, temperature etc. Cultured liquid containing the algae body which as been cultured is transferred into solid/liquid separation tank 33 through pipe 32, and then separated into algae body and supernatant fluid of algae cultured liquid. Excess algae body is returned into the digester as feedstock via storage tank 36 and return pipe 52. With respect to changing the excess algae body into methane, it is possible to improve the yield of methane by 20–50%. On the other hand, the supernatant fluid of the algae cultured liquid is charged into activated sludge aeration tank 39 through pipe 37, and separated in solid/liquid separation tank 42 into treatment finished water 43 and excess activated sludge 44 by means of an activated sludge process. The excess activated sludge is returned to digester 6 or feedstock waste storage tank 1 through return pipe 45. Oxygen 28 generated in the algae culture tank is stored in storage tank 31 through pipe 30. Furthermore, the digested sludge 14 drawn out of the storage tank 15 is charged into dehydrator 47 for dehydration, and then, the liquid is transferred to activated sludge tank 39 through pipe 55 and the dehydrated cake is dried in pre-drying equipment 48 until the water content falls below 10%, and discharged as granular digested sludge 51 which is useful as fertilizer.

The depickled water heated in depickled water layer tank 26 to a temperature of 40°–90° C. is circulated via warm water tank 53 and pipe 54 into feedstock heating equipment 4, digester 6, predrying equipment 48 of the excess digested sludge, and drying equipment 50, in a respective manner, and the recovered heat can be utilized effectively in a heat exchanger.

EXAMPLE

A feed slurry, a mixture of 0.79 kg of excess activated sludge (solid concentration 4.0%, organic concentration 3.6%) derived from city sewage treatment, 0.42 kg of the below mentioned excess algae body (solid concentration 2%, organic concentration 1.9%) and 0.053 kg of the below mentioned excess activated sludge (solid concentration 2%, organic concentration 1.9%)

from the supernatant fluid of cultured algae is charged continuously at a rate of 1.264 kg/d into a cylindrical digester having an effective volume of 20 l equipped with jacket and stirrer wing, and was digested at 35° C. under anaerobic conditions. At that time, a gas was generated at the rate of 19.4 Nl/d, the constitution of said gas was methane 54.1%, carbon dioxide 45.9% and hydrogen sulfide 0.006%. Next, the digested slurry was introduced continuously into a sedimentation tank having conical bottom of 1.5 l, and allowed to stand still for sedimentation for 24 hours, and then 0.885 kg/d of separated liquid and 0.379 kg/d of digested sludge slurry were obtained. In the separated liquid, $BOD_5$, nitrogen and phosphorus were found in a concentration 1,500 ppm, 210 ppm and 30 ppm, respectively. Next, the fermented gas was bubbled into the liquid in a vessel of $100\phi \times 400$ mm through a single nozzle of 1 mm $\phi$ while the below mentioned supernatant fluid (pH 8.5) of the algae cultured liquid and digested separated liquid were introduced, respectively at a rate of 2 l/d and 0.89 l/d, and methane gas was recovered in a concentration of 99% at the rate of 10.6 Nl/d from the top of the tower. The above mentioned supernatant fluid of the algae cultured liquid was a supernatant fluid wherein, only at the time of starting of the operation, calcium hydroxide was added into the digested separated water for adjusting the pH to 9.0. Fermented gas was introduced into the supernatant in the same manner as above-mentioned. The separated liquid was then utilized to culture the algae in the daytime only was used to wash said fermented gas, and was thereafter, separated by solid/liquid separation. In the nighttime, the supernatant fluid recovered in the daytime was used.

Next, the separated water which was used to wash the fermented gas was charged continuously into algae culture tank under an average illumination of $3 \times 10^4$ lux during the the daytime only (8:00 a.m. to about 5:00 p.m.) and utilized to culture the algae. The culture tank was $1,000(H) \times 1,000(L) \times 100$ mm(D) in size. A circulating depickled water layer having depth of 3 mm and having a transparent acrylic plate on both the upper and lower sides thereof was arranged on the top of the culture tank and was arranged at a 30° inclination facing in a southern direction. The algae cultured liquid was then charged at the same rate as the inflow rate of the separated water into a solid/liquid separation tank having conical bottom in the volume of 1 liter for separating the algae body from the supernatant fluid. 0.42 kg of the above-mentioned algae slurry (solid concentration 2%, organic concentration 1.9%) was returned to the feedstock tank. In the supernatant fluid of the algae cultured liquid, the concentration of $BOD_5$, nitrogen and phosphor was 160 ppm, 4 ppm, and 1 ppm, respectively, and the removal efficiency for each was 89%, 98% and 97%, respectively. The above-mentioned algae cultured liquid was charged into an air exposure tank of 1 liter at the rate of 0.89 l/d and subjected to an activated sludge treatment, and separated into solid and liquid, and excess activated sludge (solid concentration 2%, organic concentration 1.9%) at the rate of 0.053 kg/d was obtained. The excess activated sludge was returned as feed stock. The nature of the treated water was BOD 10 ppm, nitrogen 2 ppm and phosphor 0.3 ppm.

On the other hand, in the separated water layer, when the temperature of the water rose to 70° C., a pump was operated to pour depickled water at 20° C. therein and at the same time heated depickled water of 70° C. was caused to overflow into a storage tank of 150 l. 98 l of warm water at 70° C. on an average day (8:00 a.m. to 5:00 p.m.) was obtained. Recovered heat corresponded to 4,900 kcal.

COMPARATIVE EXAMPLE

A feed slurry which was the excess activated sludge (solid concentration 4%, organic concentration 3.6%) derived from city sewage treatment in the same batch as in the above Example was charged continuously at a rate of 0.79 kg/d into an anaerobic digester of the same construction as in the Example, and digested continuously at 35° C. under anaerobic conditions. At that time, 15.1 Nl/d of gas was generated, and the composition of said gas was methane 53%, carbon dioxide 47% and hydrogen sulfide 0.006%. Then, the digested slurry was transferred continuously into a sedimentation tank having conical bottom of 1.5 l, and allowed to stand still for sedimentation for 24 hours. Separated liquid (0.58 kg/d) and digested sludge (0.2 kg/d) were obtained. The concentration of $BOD_5$, nitrogen and phosphorus in the separated liquid were 1,200 ppm, 220 ppm and 35 ppm, respectively. Next, the separated water was diluted to five times its volume and charged a 3 liter air exposure tank at a rate of 29 l/d and subjected to activated sludge treatment, separated into solid and liquid and excess activated sludge (solid concentration 1.8%, organic concentration 1.6%) at a rate of 0.03 kg/d was obtained. Treated water containing BOD 15 ppm, nitrogen 170 ppm and phosphorus 29 ppm was obtained.

As shown in the above Example and Comparative Example, according to the present invention, (1) the yield of methane can be improved by 32%, (2) concentration of the methane can be improved from 53 vol.% (4,530 kcal/Nm$^3$) to 98 vol.% (8,380 kcal/Nm$^3$), (3) it is possible to greatly reduce the concentration of nitrogen, phosphorus in the final treated water, (4) and also it is possible to recover sun light energy, which can be utilized in the system, at a rate of $1.6 \times 10^5$ kcal/kg of dry sewage sludge.

What is claimed is:
1. A process for the treatment of organic wastes, comprising the steps:
 (a) anaerobically digesting organic wastes at a temperature of 30°–75° C. and a pH of 6.5–7.5 to obtain a digested slurry and fermentation gas containing methane or hydrogen, carbon dioxide and hydrogen sulfide;
 (b) subjecting the digested slurry obtained in step (a) to a solid/liquid separation treatment to obtain separated digested water and digested sludge;
 (c) adding calcium hydroxide to a part of the separated digested water obtained in the step (b) until the water becomes alkaline;
 (d) contacting the alkaline digested water obtained in step (c) with the fermentation gas obtained in step (a) to absorb carbon dioxide and hydrogen sulfide in the digested water to produce a purified methane gas and thereby increase the concentration of hydrogen or methane in the gas;
 (e) supplying a part of the digested water obtained in step (d) to a culturing system wherein photo-synthetic algae is cultured under illumination, thereby obtaining oxygen and algae culture, said culturing system being conducted at a pH of 7.5–9.5 and at a temperature of 30°–40° C.;
 (f) subjecting the algae culture liquid obtained in step (e) to a solid/liquid separation treatment for obtaining algae and algae culture liquid supernatant;

(g) recycling and adding part of the algae culture liquid supernatant to the alkaline digested water of step (d) for absorbing carbon dioxide and hydrogen sulfide from the fermentation gas;

(h) subjecting additional alkaline algae culture liquid supernatant obtained in step (f) to an aerobic microbial treatment to reduce the BOD; and (i) recycling algae obtained in step (f) into step (a) as feedstock for fermentation.

2. A process according to claim 1, wherein the digestion of the organic wastes under anaerobic conditions in step (a) is carried out by liquefaction fermentation with facultative anaerobic bacteria and gasification fermentation with obligatory anaerobic bacteria, thereby producing fermentation gas containing carbon dioxide and hydrogen sulfide.

3. A process according to claim 1 or 2, wherein sunlight is utilized as the illumination source in step (e) and the sunlight is filtered through a layer of depickled water, thereby warming the water layer, said warmed water being circulated to a heat-exchanger for heating the organic wastes feedstock, to a heat-exchanger for heating organic wastes in the digesting step and to a heat-exchanger for drying digested sludge.

4. A process according to claim 4, wherein said purified methane gas has a concentration exceeding 90%.

5. A process according to claim 4, wherein said purified methane gas has a concentration of about 99%.

6. A process according to claim 4, wherein said fermentation gas contains 45–70% methane and 30–55% carbon dioxide.

7. A process according to claim 4, wherein the concentration of carbonic acid in said algae culturing step is reduced and said algae culturing liquid is alkaline.

8. A process according to claim 4, wherein said purified methane gas is stored without additional desulfurization treatment.

9. A process according to claim 4, wherein oxygen is produced from said culturing step.

10. A process according to claim 9, wherein said oxygen has a purity greater than 70%.

11. A process according to claim 4, wherein sunlight is passed through a depickled water layer to illuminate the algae culture liquid.

12. A process according to claim 11, wherein heat absorbed in said depickled water layer is utilized in a heat-exchanger.

13. A process according to claim 4, wherein aqueous digested liquid from step (b) and alkaline aqueous digested liquid from step (d) are utilized as algae culture liquid in step (e).

14. A process according to claim 4, wherein calcium hydroxide is added in step (c) to adjust the pH to 7.5–10.

15. A process according to claim 4, wherein said fermentation gas is contacted with said alkaline digested liquid by blowing the gas into the liquid.

16. A process according to claim 15, wherein as a result of said blowing, the pH of the alkaline digested liquid is lowered to pH 7.2–8.0.

* * * * *